(12) United States Patent
Hwang et al.

(10) Patent No.: US 9,213,040 B2
(45) Date of Patent: Dec. 15, 2015

(54) MICROFLUIDIC CARTRIDGE FOR SEPARATING TARGET MOLECULES, AND SEPARATOR AND METHOD OF SEPARATING TARGET MOLECULES USING SAME

(75) Inventors: Kyuyoun Hwang, Yongin-si (KR); Joonho Kim, Seongnam-si (KR); Byungsoo Kim, Yongin-si (KR); Sungyoung Jeong, Yongin-si (KR); Christopher Hansung Ko, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 809 days.

(21) Appl. No.: 12/389,408

(22) Filed: Feb. 20, 2009

(65) Prior Publication Data

US 2010/0055766 A1    Mar. 4, 2010

(30) Foreign Application Priority Data

Sep. 2, 2008  (KR) .................... 10-2008-0086291

(51) Int. Cl.
*C12M 1/33* (2006.01)
*C12M 3/08* (2006.01)
*G01N 35/00* (2006.01)
(Continued)

(52) U.S. Cl.
CPC .... *G01N 35/00029* (2013.01); *B01L 3/502738* (2013.01); *B01L 3/502753* (2013.01); *B01L 9/527* (2013.01); *B01L 2200/027* (2013.01); *B01L 2200/0689* (2013.01); *B01L 2300/0681* (2013.01); *B01L 2300/0816* (2013.01); *B01L 2300/0867* (2013.01); *B01L 2400/0409* (2013.01); *B01L 2400/0677* (2013.01); *G01N 2035/00504* (2013.01)

(58) Field of Classification Search
CPC .................. B01L 3/502738; B01L 3/502753; B01L 9/527; B01L 2200/027; B01L 2200/0689; B01L 2400/0409; B01L 2400/0677; B01L 2400/0681; G01N 35/0029
USPC ................. 435/8, 259, 283.1, 306.1; 422/506
See application file for complete search history.

(56) References Cited

U.S. PATENT DOCUMENTS 4,900,446 A   2/1990  Anderson
5,006,590 A   4/1991  Takeda et al.
(Continued)

FOREIGN PATENT DOCUMENTS

KR    2004-0111165       12/2004
KR    10-2005-0030286 A   3/2005
(Continued)

OTHER PUBLICATIONS

Korean Intellectual Property Office, Communication dated Jul. 18, 2014 in counterpart Patent Application No. 10-2008-0086291.
(Continued)

*Primary Examiner* — Michael Hobbs
(74) *Attorney, Agent, or Firm* — Sughrue Mion, PLLC

(57) ABSTRACT

A microfluidic cartridge includes a capture portion capturing target material on surfaces of nonmagnetic particles; and a separating portion separating target molecules from the target material captured on the surfaces of the particles. The microfluidic cartridge is mounted on an adaptor that is rotated by a rotating unit in order to separate a fluid including the target molecules from the particles through centrifugal force.

12 Claims, 6 Drawing Sheets

(51) Int. Cl.
B01L 3/00 (2006.01)
B01L 9/00 (2006.01)

(56) References Cited

U.S. PATENT DOCUMENTS

| | | | |
|---|---|---|---|
| 6,274,308 B1 | 8/2001 | Lee et al. | |
| 6,374,684 B1 | 4/2002 | Dority | |
| 6,432,290 B1 | 8/2002 | Harrison et al. | |
| 6,706,519 B1 * | 3/2004 | Kellogg et al. | 435/287.2 |
| 2005/0026301 A1 | 2/2005 | Petithory | |
| 2006/0160208 A1 | 7/2006 | Putnam et al. | |
| 2008/0300148 A1 * | 12/2008 | Lee et al. | 506/39 |
| 2009/0143250 A1 * | 6/2009 | Lee et al. | 506/39 |

FOREIGN PATENT DOCUMENTS

| | | |
|---|---|---|
| KR | 10-2006-0079053 A | 7/2006 |
| KR | 10-0754409 B1 | 8/2007 |
| KR | 10-0763925 | 10/2007 |
| KR | 2007-0117358 | 11/2007 |
| KR | 10-0800436 | 2/2008 |
| KR | 10-0807931 | 2/2008 |
| KR | 10-0807931 A | 2/2008 |
| KR | 10-2008-0022035 A | 3/2008 |
| WO | 2004/086055 | 7/2004 |
| WO | WO 2007/024701 A2 | 3/2007 |

OTHER PUBLICATIONS

Wolfe et al. "Toward a microchip-based solid-phase extraction method for isolation of nucleic acids", Electrophoresis 2002, vol. 23, pp. 727-733.
Absolom et al. "Surface Thermodynamics of Bacterial Adhesion", Applied and Environmental Microbiology, Jul. 1983, pp. 90-97.
Chaplin, Martin. "Hofmeister Series", Water Structure and Science. <http://www1.Isbu.ac.uk/water/hofmeister_series.html>.
Germer et al. "Evaluation of the COBAS TagMan HCV Test with Automated Sample Processing Using the MagNA Pure LC Instrument". Journal of Clinical Microbiology, vol. 43, No. 1, Jan. 2005, pp. 293-298.
Park et al. "Multifunctional microvalves control by optical illumination on nanoheaters and its application in centrifugal microfluidic devices". Lab on a Chip, Vol . 7, No. 5, May 2007, pp. 557-564.

* cited by examiner

MICROFLUIDIC CARTRIDGE FOR SEPARATING TARGET MOLECULES, AND SEPARATOR AND METHOD OF SEPARATING TARGET MOLECULES USING SAME

CROSS-REFERENCE TO RELATED APPLICATIONS

This application claims the benefit of Korean Patent Application No. 10-2008-0086291, filed on Sep. 2, 2008, in the Korean Intellectual Property Office, the disclosure of which is incorporated herein in its entirety by reference.

BACKGROUND

1. Field

One or more embodiments relate to a microfluidic cartridge for separating target molecules from a sample using a centrifugal force, a separator including the microfluidic cartridge, and a separating method.

2. Description of the Related Art

Sample analysis for medical or environmental purposes is executed through a series of biochemical, chemical, and mechanical processes. Recently, technologies for diagnosing or monitoring biological samples have been actively developed. In particular, a technology for analyzing a sample through chemical and biological reactions in a chip-based device is well known. In addition, a molecular diagnosis method using a nucleic acid has been widely used in fields of infectious diseases, cancer diagnosis, and pharmacogenomics due to its high accuracy and sensitivity.

SUMMARY

One or more embodiments include a microfluidic cartridge collecting target material using fine particles, and separating fine particles from fluid including target material using a centrifugal force, a target molecule separator including the microfluidic cartridge, and a target molecule separating method.

Additional aspects and/or advantages will be set forth in part in the description which follows and, in part, will be apparent from the description, or may be learned by practice of the invention.

One or more embodiments may include a microfluidic cartridge including: a capture portion capturing target material on surfaces of nonmagnetic fine particles; and a separating portion separating target molecules from the target material captured on the surfaces of the fine particles, wherein the microfluidic cartridge is mounted on an adaptor that is rotated by a rotating unit in order to separate a fluid including the target molecules from the fine particles by the effect of the centrifugal force.

The target material may be one of target molecule including deoxyribonucleic acids (DNAs), ribonucleic acids (RNAs), proteins, peptides, antibodies, and hormones, or one of target cells including bacteria and viruses.

The capture portion may include: a sample chamber receiving a sample and including a first opening valve on an outlet of the sample chamber; a capture chamber connected to the sample chamber and including a filter on an outlet, wherein the filter does not transmit the fine particles; and a waste chamber connected to the outlet of the capture chamber and including a first closing valve on an inlet of the waste chamber. The capture portion may further include: a wash chamber that receives a wash solution, is connected to the capture chamber, and includes a second opening valve on an inlet thereof. The capture portion may further include: a second closing valve blocking the remaining sample and wash solution induced into the capture chamber.

The target material may be a target cell. The separating portion may include: a lysis solution chamber receiving a lysis solution that disrupts a cell membrane of the target cell, and including a third opening valve on an outlet of the lysis solution chamber that is connected to the capture chamber; and a separation material receiving chamber including a fourth opening valve on an inlet that is connected to the capture chamber, and receiving the fluid including the target molecules from the capture chamber.

The target material may be a target molecule. The separating portion may include: an elution solution chamber receiving an elution solution that separates the target molecules from the fine particles, and including a third opening valve on an outlet connecting to the capture chamber; and a separation material receiving chamber including a fourth opening valve on an inlet that is connected to the capture chamber, and receiving the fluid including the target molecules from the capture chamber.

One or more embodiments may include a microfluidic cartridge including: a sample chamber receiving a sample; a lysis solution/elution solution chamber receiving one of a lysis solution and an elution solution; a capture chamber connected to the sample chamber and the lysis solution/elution solution chamber, and capturing target cells/target molecules using nonmagnetic fine particles and separating the target molecules from the fine particles; a filter formed on an outlet of the capture chamber to filter the fine particles; and a separation material receiving chamber that is connected to the outlet of the capture chamber and receives a fluid including the target molecules, wherein the microfluidic cartridge is mounted on an adaptor that is rotated by a rotating unit in order to separate a fluid including the target molecules from the fine particles by the effect of the centrifugal force.

The microfluidic cartridge may further include: a wash chamber receiving a wash solution supplied to the capture chamber; a waste chamber that is connected to the outlet of the capture chamber and receives the wash solution discharged from the capture chamber; an opening valve formed on an inlet of the separation material receiving chamber to block the wash solution induced into the separation material receiving valve; and a first closing valve formed on an inlet of the waste chamber in order to block the fluid including the target molecules induced into the waste chamber.

The microfluidic cartridge may further include: a second closing valve blocking the remaining sample and wash solution induced into the capture chamber.

The fine particles may be mixed with the sample and received in the sample chamber.

The microfluidic cartridge may further include: a fine particle chip mounted in the capture chamber, wherein the fine particles are fixed on the fine particle chip.

One or more embodiments may include a target molecule separator including: the microfluidic cartridge; an adaptor including one or more mounting portions in which the microfluidic cartridge is mounted; a rotating portion rotating the adaptor; and an electromagnetic wave generator irradiating electromagnetic waves to valves of the microfluidic cartridge.

One or more embodiments may include a method of separating target molecules, the method including: loading a sample including target cells, a wash solution, and a lysis solution respectively into a sample chamber, a wash chamber, and a lysis solution chamber of a microfluidic cartridge; providing the microfluidic cartridge with nonmagnetic fine particles; mounting the microfluidic cartridge in an adaptor, and rotating the adaptor; capturing target cells on surfaces of the fine particles; supplying the wash solution to the capture chamber, and discharging impurities to a waste chamber after filtering the fine particles in the capture chamber using a filter; closing the waste chamber, and supplying the lysis solution to the capture chamber to disrupt the target cells captured by the fine particles; and opening the separation material receiving chamber, and moving fluid including target molecules separated from the target cells to the separation material receiving chamber after filtering the fine particles in the capture chamber using the filter.

One or more embodiments may include a method of separating target molecules, the method including: loading a sample including target molecules, a wash solution, and an elution solution respectively into a sample chamber, a wash chamber, and an elution solution chamber of a microfluidic cartridge; providing the microfluidic cartridge with nonmagnetic fine particles; mounting the microfluidic cartridge in an adaptor, and rotating the adaptor; capturing target molecules on surfaces of the fine particles; supplying the wash solution to the capture chamber, and discharging impurities to a waste chamber after filtering the fine particles in the capture chamber using a filter; closing the waste chamber, and supplying the elution solution to the capture chamber to separate the target molecules from the fine particles; and opening the separation material receiving chamber, and moving fluid including target molecules to the separation material receiving chamber after filtering the fine particles in the capture chamber using the filter.

The supplying of the fine particles may include: mixing the sample and the fine particles and loading the mixture to the sample chamber.

The supplying of the fine particles may include: mounting a fine particle chip in the capture chamber, wherein the fine particles are fixed on the fine particle chip.

The method may further include: blocking the remaining sample and wash solution induced into the capture chamber after supplying the wash solution to the capture chamber.

BRIEF DESCRIPTION OF THE DRAWINGS

These and/or other aspects and advantages will become apparent and more readily appreciated from the following description of the embodiments, taken in conjunction with the accompanying drawings of which.

DETAILED DESCRIPTION

Figure 1:
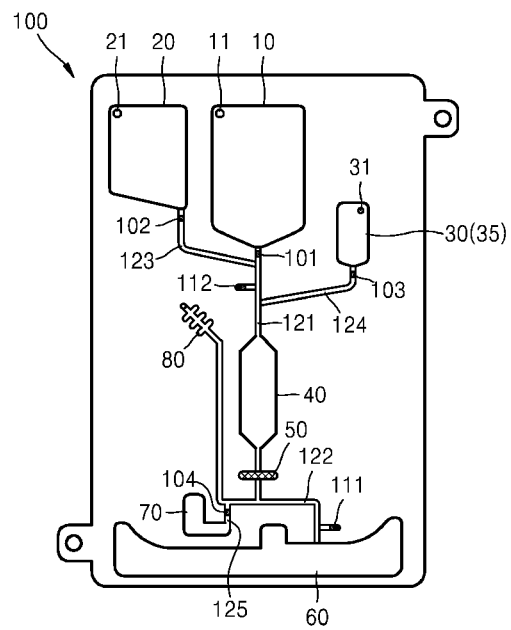
FIG. 1 is a schematic plan view of a microfluidic cartridge according to an embodiment.

Reference will now be made in detail to embodiments, examples of which are illustrated in the accompanying drawings, wherein like reference numerals refer to like elements throughout. In this regard, the present invention may be embodied in many different forms and should not be construed as being limited to the embodiments set forth herein. Accordingly, embodiments are merely described below, by referring to the figures, to explain aspects of the present invention.

FIG. 1 is a plan view of a microfluidic cartridge according to an embodiment. The microfluidic cartridge 100 includes a plurality of chambers, a plurality of channels connecting the chambers to each other, and a plurality of valves controlling flow of fluid through the plurality of channels. The above structures may be formed via solid patterns formed on one or both plates forming the microfluidic cartridge 100. The two plates may be formed of a transparent material.

The microfluidic structures in the microfluidic cartridge 100 may be functionally classified into a capture portion that captures target material including target molecules from a biological sample on surfaces of fine particles, and a separating portion separating the target molecules from the fine particles.

The biological sample may be a liquid sample with the target material including germs, blood, urine, or saliva of human being, but not limited thereto. In addition, the target molecule may be, for example, a nucleic acid, protein, peptide, antibody, or hormone. The nucleic acid may be, for example, deoxyribonucleic acid (DNA) or ribonucleic acid (RNA).

Referring to FIG. 1, the capture portion may include a sample chamber 10, a capture chamber 40, and a waste chamber 60. The sample chamber 10 receives a fluid sample. The sample chamber 10 is connected to the capture chamber 40 through a channel 121. The waste chamber 60 is connected to the capture chamber 40 through a channel 122. A first opening valve 101 may be disposed on an outlet of the sample chamber 10. The opening valve is a normally closed valve blocking flow of the fluid, and can be opened by external energy. A filter 50 is disposed on an outlet of the capture chamber 40. The filter 50 may be glass wool and blocks of fine particles, which will be described later, and transmits the fluid. A first closing valve 111 may be formed on an inlet of the waste chamber 60. The closing valve is a normally open valve that allows the fluid to flow therethrough, and can be closed by external energy. A second closing valve 112 may be connected to channel 121 between sample chamber 10 and capture chamber 40.

The chamber portion may further include a wash chamber 20 receiving wash solution. The wash chamber 20 is connected to a channel 123, and channel 121 is connected to the capture chamber 40. A second opening valve 102 may be disposed on an outlet of the wash chamber 20.

The sample chamber 10 and the wash chamber 20 may respectively include loading holes 11 and 21, through which the sample and the wash solution are respectively loaded.

The fine particles may capture target cells as a target material. In this case, the sample is a solution including target cells (for example, cell suspension, blood, or urine), and a cell membrane of the target cell is disrupted in order to extract the target molecule from the target cell. Therefore, the separating portion may include a lysis solution chamber 30 receiving a lysis solution for disrupting the cell membrane.

The fine particles may capture target molecules as a target material. In this case, the sample is a fluid including target molecules, and an elution solution is required for separating the target molecules from the fine particles instead of the disrupting operation. To do this, the separating portion may include an elution solution chamber 35 including the elution solution.

The lysis solution chamber 30/elution solution chamber 35 is connected to the capture chamber 40 through channels 124 and 121. A third opening valve 103 may be formed on an outlet of the lysis solution chamber 30/elution solution chamber 35. The lysis solution chamber 30/elution solution chamber 35 may include a loading hole 31 for injecting the lysis solution or the elution solution.

The separating portion may further include a separation material receiving chamber 70, in which a fluid including the target molecules is induced from the capture chamber 40. The separation material receiving chamber 70 is connected to the capture chamber 40 by a channel 125. A fourth opening valve 104 may be formed on an inlet of the separation material receiving valve 70.

Reference numeral 80 denotes a passive valve that is opened at a higher position than the capture chamber so that the lysis solution/elution solution can be sufficiently supplied to the capture chamber 40.

The fine particles may be, for example, silica particles or inorganic oxide material. The inorganic oxide material may be, for example, glass particles, alumina, zirconia, or titania. In the microfluidic cartridge 100 of the present embodiment, the target material is captured using silica particles. The fine particles are packed in the capture chamber 40 by centrifugal force. In addition, the sample chamber 10, the wash chamber 20, and the lysis solution chamber 30/elution solution chamber 35 may be located on opposite sides of the waste chamber 60 and the separation material receiving chamber 70 based on the capture chamber 40. Therefore, the fluid can be transferred to the sample chamber 10, the wash chamber 20, and the lysis solution chamber 30/elution solution chamber 35, the capture chamber 40, the waste chamber 60, and the separation material receiving chamber 70 using centrifugal force.

The fine particle has a surface that can specifically bind with the target material so that the target material can be captured from the blood (plasma and serum), saliva, or urine. For example, the surface of the fine particle may be a charge-reversible surface (CRS), in which polarity of charges changes according to pH of solution.

The fine particles having a CRS can be fabricated by coating surfaces of fine particles with a material having a positive ionization group (for example, amine-based) and a negative ionization group (for example, carboxy-based). The CRS may have positive charges at pH5 or lower and negative charges at higher than pH5. Fine particles having CRS can be fabricated according to the following processes.

1) Silica particles are dipped in aminopropyltriethoxysilane of 100 mM for an hour, washed using ethanol, and dried.

2) Next, the silica particles are dipped in poly(ethylene-alt-maleic anhydride) (molecular weight 100,000-500,000) of 200 mM (based on repeating unit) in N-methyl-2-pyrrolidone (NMP) for an hour, washed using NMP and ethanol, and dried.

3) In addition, the silica particles are dipped in 1-(3-aminopropyimidazole)/$H_2O$, 400 mM:600 mM) for an hour, washed using ethanol, and dried.

The fine particles may be coated with an electropositive material, or a hydrophobic material.

The electropositive material may be an aminosiliane-based material such as aminopropyltriethoxysilane or polyethyleneimine-riethoxysilane.

The hydrophobic material may be octadecyldimethyl(3-trimethoxysilylpropyl)ammonium (OTC) or tridecafluorotetrahydrooctyltriethoxysilane (DPS).

Figure 2:
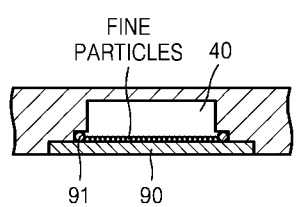
FIG. 2 is a schematic cross-sectional view showing a coupling of a chip connected to a collecting chamber, wherein fine particles are fixed to the chip.

The fine particles may be loaded into the chamber 10 together with the sample. In addition, as shown in FIG. 2, the fine particles may be fixed on a surface of a chip 90. The chip 90 may be coupled to the capture chamber 40. Reference numeral 91 is a sealing member for preventing fluid leakage.

Figure 3A:
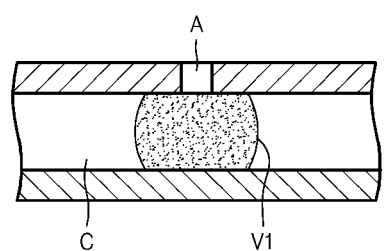
FIG. 3A is a cross-sectional view of an opening valve.
Figure 3B:
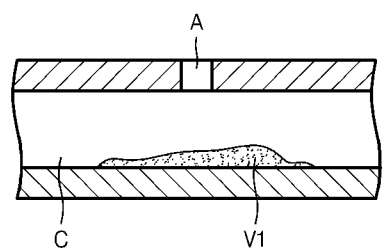
FIG. 3B is a cross-sectional view showing an opened status of the opening valve shown in FIG. 3A.

FIGS. 3A and 3B are cross-sectional views showing first through fourth opening valves 101, 102, 103, and 104 adopted in the embodiment shown in FIG. 1. The microfluidic cartridge 100 of the present embodiment may include the opening valve, which actively operates by an external driving force or external energy. The opening valve is a normally-closed valve, which blocks the channel C so that the fluid cannot flow as shown in FIG. 3A before absorbing electromagnetic wave energy.

The opening valve may include a valve material V1 that is in solid status at room temperature. The valve material V1 is loaded into a region through a loading hole A in the melted status, and then, solidificated to block the channel C as shown in FIG. 3A. The valve material V1 is melted at a high temperature and moves in a space in the channel C, and then, is coagulated again after opening the channel C as shown in FIG. 3B.

The energy irradiated from the outside may be in the form of electromagnetic waves, and the energy source may be a laser light source irradiating laser beams or a light emitting diode or a Xenon lamp irradiating visible rays or infrared rays. In particular, when the energy source is a laser light source, the laser light source may include at least one laser diode. The external energy source may be selected according to wavelengths of electromagnetic waves that can be absorbed by heat generating particles included in the valve material V1.

The valve material V1 may be a thermoplastic resin such as cyclic olefin copolymer (COC), polymethylmethacrylate (PMMA), polycarbonate (PC), polystyrene (PS), polyoxymethylene (POM), perfluoroalkoxy (PFA), polyvinylchloride (PVC), polypropylene (PP), polyethylene terephthalate (PET), polyetheretherketone (PEEK), polyamide (PA), polysulfone (PSU), and polyvinylidene fluoride (PVDF).

In addition, a phase transition material that is in a solid state at room temperature may be used as the valve material V1. The phase transition material may be wax. When the wax is heated, the wax is melted to a liquid state, and the volume of the wax expands. The wax may be paraffin wax, microcrystalline wax, synthetic wax, or natural wax. The phase transition material may be gel or thermosetting resin. The gel may be polyacrylamide, polyacrylates, polymethacrylates, or polyvinylamides.

A plurality of fine heat generating particles, which generate heat by absorbing electromagnetic wave energy, may be dispersed in the valve material V1. Each of the fine heat generating particles has a diameter of 1 nm to 100 μm so as to freely pass through a channel having a depth of about 0.1 mm and a width of 1 mm. When the electromagnetic wave energy is supplied by the laser beam, the temperature of the fine heat generating particles rapidly rises so that the fine heat generating particles generate heat, and the fine heat generating particles are evenly dispersed in the wax. To have the above property, each of the fine heat generating particles may include a core having a metal component and a hydrophobic surface structure. For example, the fine heat generating particle may have a molecular structure including a core formed of iron (Fe) and a plurality of surfactants surrounding the Fe by being bounded with Fe. The fine heat generating particles may be preserved in a dispersed form in carrier oil. The carrier oil may be hydrophobic so that the fine heat generating particles having the hydrophobic surface structure can be evenly dispersed therein. The carrier oil, in which the fine heat generating particles are dispersed, is mixed with the melted phase transition material, and then, the mixture is loaded into the channel C and coagulated to block the channel C.

The fine heat generating particles are not limited to the above described polymer particles, and may be formed as quantum dots or magnetic beads. In addition, the fine heat generating particles may be fine metal oxides such as $Al_2O_3$, $TiO_2$, $Ta_2O_3$, $Fe_2O_3$, $Fe_3O_4$, or $HfO_2$. On the other hand, the opening valve may be formed of the phase transition material without including the fine heat generating particles.

Figure 4A:
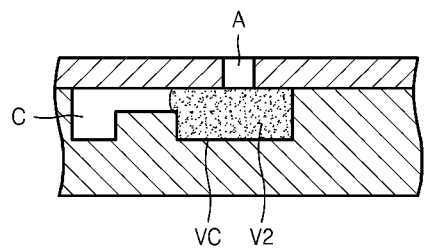
FIG. 4A is a cross-sectional view of a closing valve.
Figure 4B:
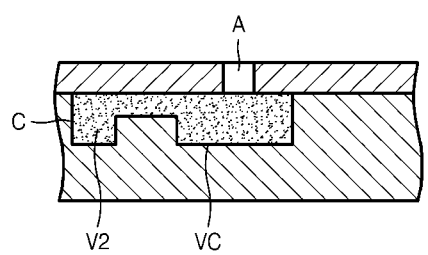
FIG. 4B is a cross-sectional view showing a closed status of the closing valve shown in FIG. 4A.

FIGS. 4A and 4B are cross-sectional views showing examples of the first and second closing valves 111 and 112 shown in FIG. 1. The microfluidic cartridge 100 of the present embodiment may use the closing valve which is a normally-open valve that actively closes when receiving a driving force or energy from the outside. The closing valve opens the channel C so that the fluid can flow before absorbing the electromagnetic wave energy.

The closing valve includes a channel C, a valve chamber VC connecting to a part of the channel C, and a valve material V2 filled in the valve chamber VC through the loading hole A. The valve material V2 may be the same as the valve material V1. As shown in FIG. 4A, before the external energy is supplied, the valve material V2 exists in the valve chamber VC, and the channel C is in the open status. Then, when the external energy is supplied to the valve material V2, the valve material V2 is melted and expanded to be induced into the channel C and is coagulated again to block the flow of the fluid in the channel C, as shown in FIG. 4B.

Figure 5:
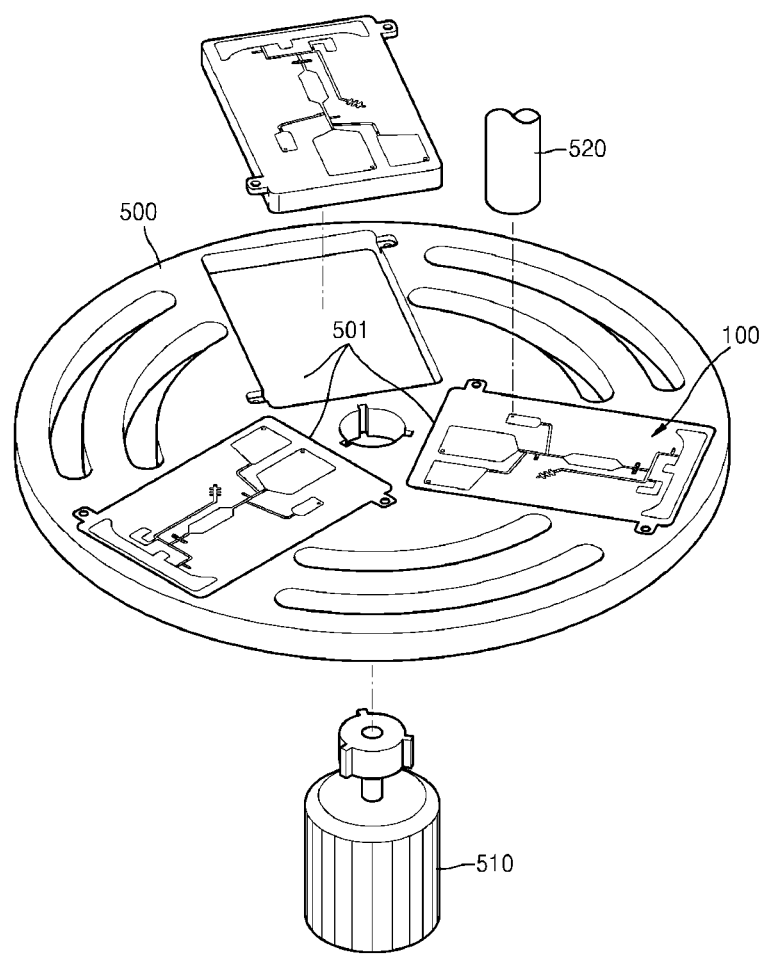
FIG. 5 is a schematic perspective view of a separator according to an embodiment.

FIG. 5 is a diagram showing a separator for separating target molecules using the microfluidic cartridge 100 shown in FIG. 1. The separator includes an adaptor 500 and a rotating portion 510. The adaptor 500 includes one or more mounting portions 501 to which the microfluidic cartridge 100 can be mounted. The rotating portion 510 rotates the adaptor 500 in order to move the fluid to a predetermined position in the microfluidic cartridge 100. An electromagnetic wave generator 520 irradiates laser beams, for example. The electromagnetic wave generator 520 may be moved in a radial direction of the microfluidic cartridge 100. The rotating portion 510 makes the microfluidic cartridge 100 stop at a predetermined position so that the plurality of valves face the electromagnetic wave generator 520. The rotating portion 510 may include a motor drive device that can control the angular position of the microfluidic cartridge 100, although the motor drive device is not shown in the drawings. For example, the motor drive device may include a step motor or a servo motor. On the other hand, an analyzing device may further include an optical detector (not shown) for optically detecting the separated nucleic acid. The electromagnetic wave generator 520 may supply energy to the capture chamber 40 to help the disruption of the cell membrane of the target cell.

A method of capturing target cells using fine particles, disrupting the target cell (for example, bacteria), and separating the target molecule (for example, nucleic acid) will be described as follows according to an embodiment of the present invention.

A liquid sample including fine particles and bacteria is loaded into the sample chamber 10. For example, a mixed solution of urine including bacteria and sodium acetate of pH3, 100 mM is loaded into the sample chamber 10. The wash solution is loaded into the wash chamber 20. For example, Tris-HCL of pH9 and 10 mM is loaded into the wash chamber 20. The lysis solution is loaded into the lysis solution chamber 30. For example, NaOH of 0.01N is loaded into the lysis solution chamber 30. The fine particles may have the CRS, electropositive surfaces, or hydrophobic surfaces.

Next, as shown in FIG. 5, the microfluidic cartridge 100 is mounted on the adaptor 500. The rotating portion 510 repeatedly rotates the adaptor 500 in clockwise/counter clockwise directions to mix the fine particles and the cell suspension. Accordingly, the target cells are captured on the surfaces of the fine particles in the sample chamber 10.

Figure 6:
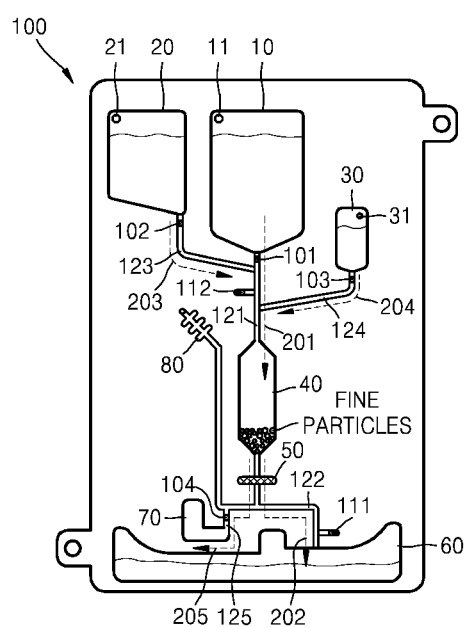
FIG. 6 is a diagram for explaining a target molecule separating method in which target cells are collected using fine particles.

When the electromagnetic waves are irradiated to the first opening valve 101 by the electromagnetic wave generator 520, the valve material V1 is melted and the channel 121 is opened. The adaptor 500 may be rotated for three minutes at 4500 rpm. Due to the centrifugal force, the liquid sample, in which the fine particles are dispersed, is moved to the capture chamber 40 as denoted by an arrow 201 shown in FIG. 6. At this time, the bacteria are captured on surfaces of the fine particles. Since the fine particles do not pass through the filter 50, the fine particles, on which the bacteria are captured, are packed in the capture chamber 40, and only the fluid can pass through the filter 50. The channel 122 is in the open status. In addition, the channel 125 is closed by the fourth opening valve 104. Therefore, the fluid passing the filter 50 is moved to the waste chamber 60 as denoted by an arrow 202 shown in FIG. 6.

Next, a process for removing impurities on the fine particles may be performed in the capture chamber 40. When the electromagnetic waves are irradiated to the second opening valve 102 by the electromagnetic wave generator 520, the valve material V1 of the second opening valve 102 is melted and the channel 123 is opened. The adaptor 500 may be rotated for one minute at about 3500 rpm. The wash solution received in the wash chamber 20 is moved to the capture chamber 40 by the centrifugal force, as denoted by an arrow 203 shown in FIG. 6. The fine particles in the capture chamber 40 are washed by the wash solution. The wash passing through the filter 50 is moved to the waste chamber 60.

Next, a lysis process of the bacteria cells captured on the surfaces of the fine particles may be performed. To do this, the electromagnetic waves are irradiated onto the first closing valve 111. Then, the valve material V2 in the first closing valve 111 is melted and induced into the channel 122. When the valve material V2 is coagulated in the channel 122, the channel 122 is blocked. In addition, the electromagnetic waves can be irradiated to the second closing valve 112 to block the channel 121 so that the remaining impurities are not induced into the capture chamber 40 from the sample chamber 10. When the electromagnetic waves are irradiated onto the third opening valve 103 by the electromagnetic wave generator 520, the valve material V1 of the third opening valve 103 is melted and the channel 124 is opened. The adaptor 500 may be rotated for thirty seconds at 2500 rpm and thirty seconds at 3500 rpm. The lysis solution received in the lysis solution chamber 30 is moved to the capture chamber 40 by the centrifugal force, as denoted by the arrow 204 shown in FIG. 6. A passive valve 80 makes the fine particles sufficiently soaked with the lysis solution. The cell membranes of the bacteria captured on the surfaces of the fine particles are damaged, and the nucleic acid in the cell is exposed.

In order to help the lysis operation of the cells, for example, in order to transfer the thermal energy to the capture chamber 40, the electromagnetic wave may be irradiated, or a resistance heating of the adaptor 500 may be performed. The efficiency of the cell membrane lysis can be increased when the thermal energy is transferred.

Next, when the electromagnetic waves are irradiated onto the fourth opening valve 104 by the electromagnetic wave generator 520, the valve material V1 of the fourth opening valve 104 is melted and the channel 125 is opened. When the adaptor 500 is rotated, the fluid including the nucleic acid received in the capture chamber 40 is moved to the separation material receiving chamber 70 by the centrifugal force, as denoted by an arrow 205 shown in FIG. 6.

As described above, according to the method of separating the nucleic acid of the present embodiment, the non-magnetic fine particles are packed in the capture chamber 40 due to the centrifugal force, and the fluid including the nucleic acid can be separated.

In the above described method of separating the target molecules, the fine particles are loaded into the sample chamber 10 with the liquid sample, and then, the target molecules are separated. However, the scope of the present invention is not limited thereto. As shown in FIG. 2, when the chip 90, on which the fine particles are fixed, is coupled to the capture chamber 40, only the liquid sample may be loaded into the sample chamber 10. Processes are the same as the above described method except that the capture of the target cells is performed in the capture chamber 40 after moving the liquid sample to the capture chamber 40.

A method of capturing the target molecules (for example, nucleic acid) using the fine particles and separating the nucleic acid from the fine particles will be described as follows according to an embodiment of the present invention.

A sample including fine particles and nucleic acid is loaded into the sample chamber 10. The sample may include a biochemical buffer solution, which can provide an environment condition of pH5 of lower, so that the surfaces of fine particles can capture the nucleic acid, for example. A solution, which is made by mixing bacteria cells lysate with sodium acetate solution of 100 mM and pH3 to be pH5 or lower, is loaded into the sample chamber 10. The wash solution, for example, Tris-HCl of pH9 and 10 mM, is loaded into the wash chamber 20. An elution solution, for example, Tris-HCl-EDTA buffer of pH9 and 10 mM, is loaded into the elution solution chamber 35. The fine particles may have the above described CRS.

Next, as shown in FIG. 5, the microfluidic cartridge 100 is mounted in the adaptor 500. The adaptor 500 is repeatedly rotated in the clockwise/counter clockwise directions so as to mix the sample and the fine particles in the sample chamber 10. Accordingly, the fine particles capture the nucleic acid on the surfaces thereof in the sample chamber 10.

Figure 7:
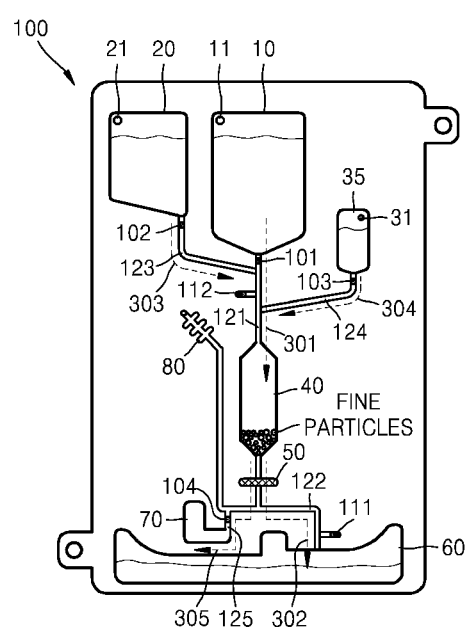
FIG. 7 is a diagram for explaining a target molecule separating method in which target molecules are directly collected using fine particles.

When the electromagnetic waves are irradiated onto the first opening valve 101 by the electromagnetic wave generator 520, the valve material V1 of the first opening valve 101 is melted and the channel 121 is opened. When the adaptor 500 is rotated, the sample is moved to the capture chamber 40 by the centrifugal force, as denoted by an arrow 301 shown in FIG. 7. Since the fine particles cannot pass through the filter 50, the fine particles on which the nucleic acid is captured are packed in the capture chamber 40, and only the fluid passes through the filter 50. The channel 122 is in the open status. In addition, the channel 125 is blocked by the fourth opening valve 104. Therefore, the solution passing the filter 50 is moved to the waste chamber 60, as denoted by an arrow 302 shown in FIG. 7.

Next, a process of removing the impurities in the capture chamber 40 may be performed. When the electromagnetic waves are irradiated onto the second opening valve 102 by the electromagnetic wave generator 520, the valve material V1 of the second opening valve 102 is melted and the channel 123 is opened. When the adaptor 500 is rotated, the wash solution received in the wash chamber 20 is moved to the capture chamber 40 by the centrifugal force, as denoted by an arrow 303 shown in FIG. 7. The fine particles are washed by the wash solution. The wash solution passing through the filter 50 is moved to the waste chamber 60.

In addition, a process of separating the nucleic acid captured on surfaces of the fine particles from the fine particles may be performed. To do this, the electromagnetic waves are irradiated to the first closing valve 111. Then, the valve material V2 of the first closing valve 111 is melted and the valve material V2 is induced into the channel 122. When the valve material V2 is coagulated in the channel 122, the channel 122 is blocked. In addition, the electromagnetic waves may be irradiated to the second closing valve 112 to close the channel 121 so that the impurities are not induced into the capture chamber 40 from the wash chamber 20 and the sample chamber. When the electromagnetic waves are irradiated onto the third opening valve 103 by the electromagnetic wave generator 520, the valve material V1 in the third opening valve 103 is melted and the channel 124 is opened. When the adaptor 500 is rotated, the elution solution received in the elution solution chamber 35 is moved to the capture chamber 40 by the centrifugal force, as denoted by an arrow 304 shown in FIG. 7. The passive valve 80 makes the fine particles sufficiently soaked in the elution solution. The charge on the surface of the fine particles is changed by the elution solution, and the nucleic acid is separated from the fine particles.

Next, when the electromagnetic waves are irradiated to the fourth opening valve 104 by the electromagnetic wave generator 520, the valve material V1 of the fourth opening valve 104 is melted and the channel 125 is opened. When the adaptor 500 is rotated, the fluid including the nucleic acid received in the capture chamber 40 is moved to the separation material receiving chamber 70 by the centrifugal force, as denoted by an arrow 305 shown in FIG. 7. The fine particles 50 are blocked by the filter 50, and packed in the capture chamber 40.

As described above, according to the method of separating the nucleic acid of the present invention, non-magnetic fine particles are packed in the capture chamber 40 due to the centrifugal force, and the fluid including the nucleic acid can be separated.

In the above described method, the fine particles are loaded into the sample chamber 10 with the sample including the nucleic acid, and then, the nucleic acid is separated. However, the scope of the present invention is not limited thereto. As shown in FIG. 2, when the chip 90 on which the fine particles are fixed is coupled to the capture chamber 40, the sample including the nucleic acid is only loaded into the sample chamber 10. Other processes are the same as the above described method except that the capture of nucleic acid using the fine particles is performed in the capture chamber 40 after the sample is moved to the capture chamber 40.

While aspects of the present invention have been particularly shown and described with reference to differing embodiments thereof, it should be understood that these exemplary embodiments should be considered in a descriptive sense only and not for purposes of limitation. Descriptions of features or aspects within each embodiment should typically be considered as available for other similar features or aspects in the remaining embodiments.

Thus, although a few embodiments have been shown and described, it would be appreciated by those of ordinary skill in the art that changes may be made in these embodiments without departing from the principles and spirit of the invention, the scope of which is defined in the claims and their equivalents.

What is claimed is:

1. A microfluidic cartridge comprising:
a sample chamber, which contains a sample including a target material, the sample chamber including a first opening valve on an outlet of the sample chamber;
a capture chamber, which contains nonmagnetic particles which capture the target material on surfaces of the nonmagnetic particles, connected to the sample chamber and including a filter on an outlet of the capture chamber, wherein the filter does not transmit the nonmagnetic particles;
a waste chamber connected to the outlet of the capture chamber and including a first closing valve on an inlet of the waste chamber;
a solution chamber, which contains a solution which separates target molecules from the target material captured on the surfaces of the nonmagnetic particles, including a third opening valve on an outlet of the solution chamber that is connected to the capture chamber; and
a separation material receiving chamber including a fourth opening valve on an inlet that is connected to the capture chamber, and which receives a fluid including the target molecules from the capture chamber,
wherein the microfluidic cartridge is mounted on an adaptor that is rotated by a rotating unit in order to separate the fluid including the target molecules from the nonmagnetic particles by the effect of centrifugal force.

2. The microfluidic cartridge of claim 1, wherein the target material is at least one target molecule selected from a group consisting of a deoxyribonucleic acid (DNA), ribonucleic acid (RNA), protein, peptide, antibody, and hormone, or at least one target cell selected from a group consisting of a bacterium and virus.

3. The microfluidic cartridge of claim 1, further comprising:
a wash chamber that receives a wash solution, is connected to the capture chamber, and includes a second opening valve on an inlet thereof.

4. The microfluidic cartridge of claim 3, further comprising:
a second closing valve blocking a remaining sample in the sample chamber and remaining wash solution in the wash chamber induced into the capture chamber.

5. The microfluidic cartridge of claim 4, wherein the target material is a target cell.

6. The microfluidic cartridge of claim 5, wherein the solution chamber is a lysis solution chamber receiving a lysis solution that disrupts a cell membrane of the target cell.

7. The microfluidic cartridge of claim 6, further comprising:
a particle chip mounted in the capture chamber, wherein the particles are fixed on the particle chip.

8. The microfluidic cartridge of claim 4, wherein the target material is the target molecules.

9. The microfluidic cartridge of claim 8, wherein the solution chamber is an elution solution chamber receiving an elution solution that separates the target molecules from the nonmagnetic particles.

10. The microfluidic cartridge of claim 9, further comprising:
a fine particle chip mounted in the capture chamber, wherein the fine particles are fixed on the fine particle chip.

11. A target molecule separator comprising:
the microfluidic cartridge of claim 1;
an adaptor including one or more mounting portions in which one or more microfluidic cartridges are mounted;
a rotating portion rotating the adaptor; and
an electromagnetic wave generator irradiating electromagnetic waves to valves of the microfluidic cartridge.

12. The target molecule separator of claim 11,
wherein the microfluidic cartridge further comprises opening valves, and closing valves;
wherein said target material is contained in a liquid sample;
wherein the electromagnetic wave generator irradiates electromagnetic waves to the opening valves and to the closing valves of the microfluidic cartridge;
wherein the target material comprises target molecules;
wherein the microfluidic cartridge is mounted on the adaptor;
wherein the adaptor is rotated by the rotating portion to separate a fluid including the target molecules from the particles using a centrifugal force; and
wherein the opening valves are opened by irradiation with electromagnetic waves and the closing valves are closed by irradiation with electromagnetic waves in order to control fluid movement.

* * * * *